United States Patent [19]
Postaire et al.

[11] Patent Number: 6,045,809
[45] Date of Patent: *Apr. 4, 2000

[54] PHARMACEUTICAL COMPOSITIONS CONTAINING A SUPEROXIDE DISMUTASE

[75] Inventors: Eric Postaire, Vanves; Corinne Regnault, Antony; Monique Rock-Arveiller, Palaiseau; Valérie Stella, Claye-Souilly; Michel Brack, Bois-Colombes; Jacques Sauzieres, Saint Remy les Chevreuses, all of France

[73] Assignee: Institut de Recherches Franctales, Boise-Colombes, France

[*] Notice: This patent issued on a continued prosecution application filed under 37 CFR 1.53(d), and is subject to the twenty year patent term provisions of 35 U.S.C. 154(a)(2).

[21] Appl. No.: 08/860,965

[22] PCT Filed: Jan. 12, 1996

[86] PCT No.: PCT/FR95/00055

§ 371 Date: Sep. 12, 1997

§ 102(e) Date: Sep. 12, 1997

[87] PCT Pub. No.: WO96/21462

PCT Pub. Date: Jul. 18, 1996

[30] Foreign Application Priority Data

Jan. 12, 1995 [FR] France .................................. 95 00309

[51] Int. Cl.$^7$ .............................. A61K 38/43; A61K 9/08
[52] U.S. Cl. ............................ 424/400; 424/94.3; 514/21
[58] Field of Search .................................. 424/450, 489, 424/400, 94.3; 514/21

[56] References Cited

U.S. PATENT DOCUMENTS

| | | | |
|---|---|---|---|
| 5,019,400 | 5/1991 | Gombotz | 424/497 |
| 5,271,961 | 12/1993 | Mathiowitz | 427/213.31 |
| 5,665,778 | 9/1997 | Semenic | 514/613 |

FOREIGN PATENT DOCUMENTS

| | | |
|---|---|---|
| 0292964 | 11/1988 | European Pat. Off. |
| 0342620 | 11/1989 | European Pat. Off. |

*Primary Examiner*—Gollamudi S. Kishore
*Attorney, Agent, or Firm*—Lowe Hauptman Gopstein Gilman & Berner

[57] ABSTRACT

Novel pharmaceutical compositions that are particularly suitable for oral administration of superoxide dismutases (SODs) and that have good bioavailability and therapeutic efficacy. These compositions are made up of a combination of a superoxide dismutase and at least one lipids or proteins. The lipids are exemplified by ceramides, and the proteins are exemplified by prolamines or polymer films based on such prolamines. A pharmaceutically acceptable vehicle can also be included in the composition.

10 Claims, 17 Drawing Sheets

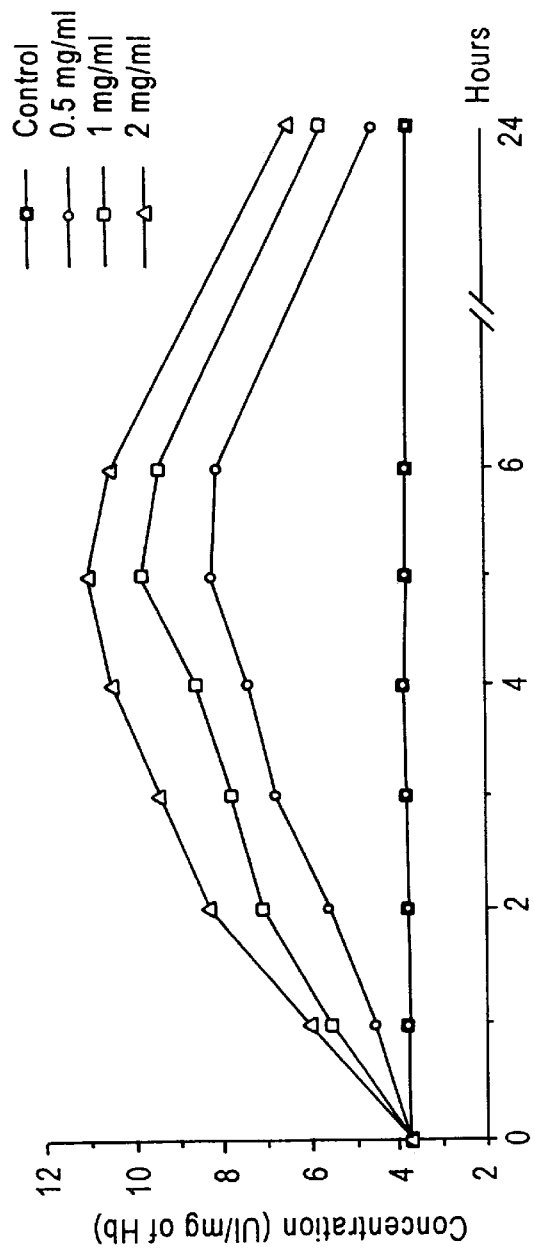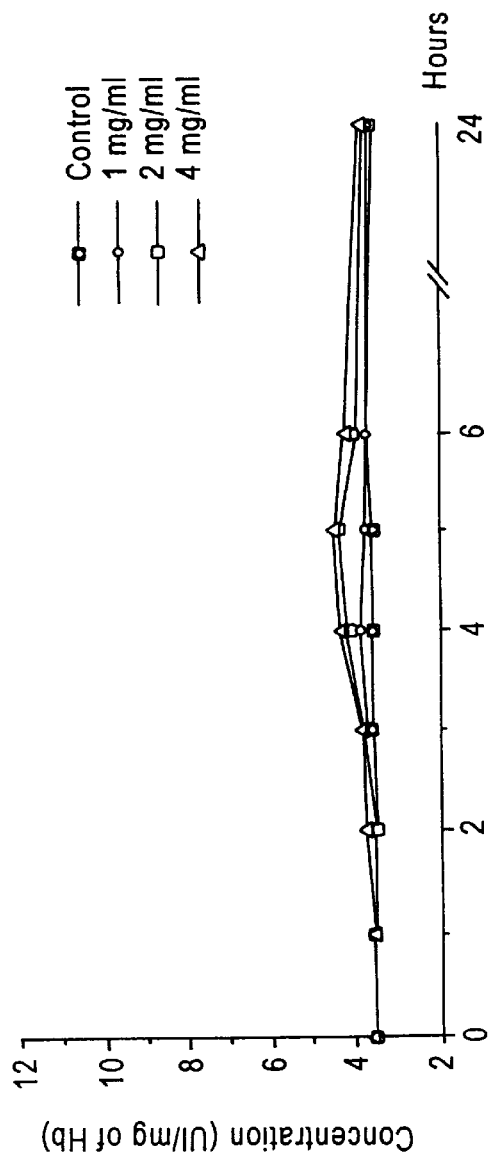
FIG. 3
FIG. 4

PHARMACEUTICAL COMPOSITIONS CONTAINING A SUPEROXIDE DISMUTASE

This application is a 371 of PCT/FR95/00055 filed Jan. 12, 1996.

The present invention relates to novel pharmaceutical compositions which are particularly suitable for the oral administration of superoxide dismutase (SOD), ensuring that it has a good bioavailability and therapeutic efficacy.

Since their characterization in 1968 by McCord and Fridovich (J. Biol. Chem., 1969, 244, 6049–6055), superoxide dismutases have been studied in the treatment of numerous diseases; superoxide dismutase is in fact an enzyme which promotes removal of the superoxide radical $(.O_2^-)$ by dismutation and therefore constitutes a system for providing protection from the deleterious effects of this radical, which is capable of forming in vivo from atmospheric oxygen. Consequently this enzyme plays a fundamental role in preventing the toxic effects which could result from exposure of the cells and the organism to an oxygenated atmosphere in which oxygen (a biradical) loses an unpaired electron (reduction).

As free radicals are involved in numerous diseases, the use of SOD in therapeutics has been recommended in different inflammatory processes (rheumatism and fibrosis in particular), viral processes (HIV infection in particular) and toxic conditions associated with the presence of substantial amounts of oxygen (central nervous system, ischemia, non-vascular gastrointestinal disorders, eye disorders or control of the undesirable effects of anticancer treatments) (Greenwald R. A., *Free Radical Biol. Med.*, 1990, 8, 201–209).

The free forms of SOD which have been tested are Cu,Zn-SOD (vegetable origin or animal origin: bovine, rat or human), Mn-SOD (human, vegetable, algal origin), Fe-SOD and recombinant SODS.

The plasmatic half-lives of native SODs are very variable (of the order of a few minutes for Cu,Zn-SOD; of the order of several hours for Mn-SOD, for example).

Different modified forms for parenteral administration have been proposed for increasing the plasmatic half-life of these SODs; modified forms which may be mentioned are SODs conjugated with polyethylene glycol (SOD-PEG), SODs conjugated with heparin (SOD-heparin), SODs conjugated with albumin (SOD-albumin), SOD polymers or copolymers and liposomal SODs.

However, these different SODs have the major disadvantage of being very poorly absorbed when administered orally.

Consequently the Applicant set out to develop galenic forms capable of affording an effective absorption of SOD by oral administration, said mode of administration being particularly valuable for the majority of the above-mentioned diseases to be treated.

SUMMARY OF THE INVENTION

The present invention relates to pharmaceutical compositions which are characterized in that they essentially comprise a combination of a superoxide dismutase and at least one compound selected from the group consisting of lipids and proteins and optionally one or more pharmaceutically acceptable vehicles, said compositions being particularly suitable for oral administration.

In one advantageous embodiment of said compositions, said lipids are selected from plant lipids, preferably from the group consisting of ceramides, phospholipids, tylacoids and diacylglycerols.

In another advantageous embodiment of said compositions, said proteins are selected from plant proteins, preferably from the group consisting of prolamines and polymer films based on said prolamines.

Liposomes may be mentioned among the preferred vehicles which may be associated with the compositions.

In another advantageous embodiment of said composition, said ceramides (or N-acylsphingosines) are of synthetic, animal or vegetable origin, preferably of vegetable origin, and are N-acyl fatty acid derivatives of sphingosine of the formula

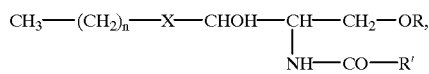

in which n is between 5 and 15, preferably between 12 and 15,

X is —CH=CH— or —CHOH—,

R is a hydrogen atom or a sugar (glucose, galactose) and

R' is a $C_3$–$C_{30}$ alkyl group.

Advantageously said ceramides of vegetable origin are preferably derived from cereals (flours), especially wheat, and have the following formula:

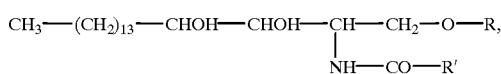

in which

R is a hydrogen atom or a glucose and

R' is as defined above.

Such plant ceramides (glycosylated or non-glycosylated) can be obtained in particular by the process described in international patent application PCT WO 92/00182 in the name of Laboratoires INOCOSM.

In another advantageous embodiment of said compositions, the prolamines are preferably of vegetable origin, can be obtained from different cereals, especially from wheat, rye, barley, oats, rice, millet and maize, preferably from wheat (gliadin), and are preferably native (i.e. non-denatured) prolamines derived either from the flour or from the fresh gluten of one of the above-mentioned cereals.

In yet another advantageous embodiment of said compositions, the polymer films based on prolamine preferably consist of a hydrophobic polymer comprising at least one prolamine of vegetable origin, at least one plasticizer selected from the group consisting of carbohydrates, preferably polyols and esters such as phthalates, adipates, sebacates, phosphates, citrates, tartrates and malates, the ratio of prolamine to plasticizer being between 2:1 and 2:0.5, and 5 to 30% of at least one solvent selected from monools, diols and water, and can be obtained by evaporation of at least part of the solvent present in a starting composition comprising between 40 and 80% of at least one prolamine dissolved in an aqueous-alcoholic solvent with an alcohol titre of between 40 and 80%, and at least one plasticizer, the ratio of plasticizer to alcoholic prolamine solution being between 0.10:1 and 0.50:1, preferably between 0.20:1 and 0.23:1, until a homogeneous solution of greater or lesser thickness is obtained.

Such polymer films based on prolamine can take the form either of a gel or of a flexible or brittle dry film, i.e. a more or less plastic film, depending on the degree of evaporation of the solvent.

Unexpectedly, a composition according to the invention is particularly suitable for the oral administration of SOD because it significantly increases the bioavailability of the SOD compared with that obtained with the SOD compositions of the prior art.

Again unexpectedly, the composition according to the invention, namely SOD+polymer film based on prolamine (preferably gliadin):

protects the SOD at acid pH (gastric medium) and constitutes a sustained release form.

BRIEF DESCRIPTION OF THE DRAWINGS

In addition to the foregoing provisions, the invention also comprises other provisions which will become apparent from the following description referring to Examples of how to carry out the process forming the subject of the present invention, and to the attached drawings, in which:

FIGS. 1 to 3 show the erythrocyte concentrations obtained after the subcutaneous administration of different forms of SOD (free, liposomal, according to the invention: with ceramides);

FIGS. 4 to 7 show the erythrocyte concentrations obtained after the oral administration of different forms of SOD;

Figure 1:
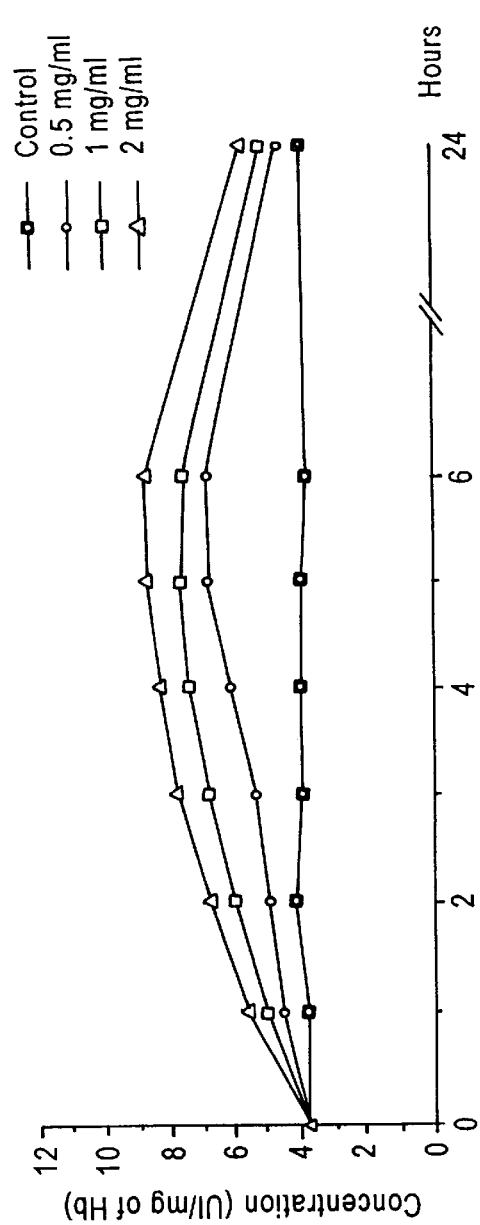

It must be clearly understood, however, that these Examples are given solely in order to illustrate the subject of the invention, without in any way implying a limitation.

DETAILED DESCRIPTION OF THE INVENTION

EXAMPLE 1

Composition According to the Invention: SOD+ polymer based on gliadin

1. Method of incorporating the SOD in the gliadin

Composition of the gliadin+SOD formulation:

| n° | Name | Amount |
|---|---|---|
| 1 | Aqueous-alcoholic solvent (50% v/v of ethanol) | 18.25 ml |
| 2 | Sorbitol | 1.575 g |
| 3 | Glycerol | 0.675 g |
| 4 | Gliadin | 4.5 g |
| 5 | SOD | 1 ml* |

*solutions containing 4 mg/ml, 2 mg/ml, 1 mg/ml

Preparative protocol.

Introduce the aqueous-alcoholic solvent into a small beaker placed in a bath thermostated at 40° C., with mechanical stirring. Then add compounds 2, 3, 4 and 5 in order. After each addition, stir until the compounds have completely dissolved.

The mixture is heated and stirred in order to reduce the gliadin-gliadin hydrophobic interactions and hence increase the solubility of the gliadin.

The glycerol is used as a moisturizer and the sorbitol as a stabilizer and plasticizer. The mixture obtained is viscous, sticky and brownish in colour.

2. Formulation of the mixture obtained in 1.

To obtain a composition according to the invention in the form of tablets, for example, the pasty mixture obtained is spread on an appropriate support (Teflon, polypropylene, glass or stainless steel support) and the solvent is evaporated off either at 24° C. and a relative humidity of 60% for about forty hours, or at 60° C. and a relative humidity of 2% for about twenty hours, or at 37° C.: a lamp is placed 20 cm from the film for a few hours (2–10 h).

The dry film obtained is then cut up and ground to permit the preparation of tablets.

EXAMPLES 2 AND 3

| | Formulation (w/w) | Particle size (nm) | Poly-dispersity | Percentage encapsulation of the SOD |
|---|---|---|---|---|
| EXAMPLE 2 (SOD + liposomes) | DSPC/CH0/stearylamine/- (14/7/4/0) | 234 | 3 | 36.2% |
| EXAMPLE 3 (SOD + ceramides at different concentrations): | DSPC/CHO/stearylamine/PC (14/7/4/1) | 244 | 4 | 48.2% |
| | DSPC/CHO/stearylamine/PC (14/7/4/4) | 258 | 3 | 36.5% |
| | DSPC/CHO/stearylamine/PC (14/7/4/7) | 241 | 3 | 31.9% |
| | DSPC/CHO/stearylamine/PC (14/7/4/14) | 269 | 4 | 26.6% |

In this Table the abbreviation DSPC denotes distearoylphosphatidylcholine, the abbreviation CHO denotes cholesterol and the abbreviation PC denotes plant ceramide.

Example 2 corresponds to a composition of the prior art; Example 3 corresponds to an SOD+ceramide composition according to the invention, largely encapsulated in liposomes (DSPC/CHO/stearylamine).

The liposomes are obtained by the process described in European patent application 0 274 961 or European patent application 0 349 429 and have a good homogeneity, as shown in the polydispersity column.

EXAMPLE 4

Comparative Pharmacokinetic Study After the Subcutaneous and Oral Administration of Compositions Based on SOD The kinetics of the plasmatic SOD are analyzed in anaesthetized rats after the oral or subcutaneous administration of free SOD, liposomal SOD or SOD in the form of a composition according to the invention.

Materials

Animals:

The rats used are male OFA, Sprague-Dawley rats which are devoid of pathogenic germs, weigh 300 to 400 g and are not of the same blood type (IFFA CREDO breed). They are kept for 3 weeks after arrival at the animal house in order to avoid any stress associated with the change of environment, and are placed on a water diet 16 to 18 hours before the experiment.

Equipment used:

5 ml disposable graduated plastic syringes for the gavage (1 per dose), the subcutaneous injection and the anaesthetic, 1 ml syringes for the anaesthetic, Straight 85/14 gavage cannulas (1 per dose), Disposable 25/0.5 needle for the anaesthetic, Crystallizers for isolating the rats while they pass into unconsciousness, Surgical accessories for catheterization:
  PE50 catheters (Becton-Dickinson)
  tracheal cannulas for assisted breathing
  1-way taps (Vygon).

Anaesthetizing solution:

The anaesthetic used is thiopental (Nesdonal®). It is administered at a rate of 50 mg/kg body weight.

The solution is prepared immediately before use.

Heparin solution:

Heparinated PVP (polyvinylpyrrolidone) 500 mg/ml+200 IU of heparin in NaCl 0.9%.

Solutions used for the study:

Oral administration:
  bovine erythrocyte SOD (Allerbiodose®) 1–2–4 mg/ml, in NaCl 0.9%,
  NaCl 0.9% (control),
  bovine erythrocyte SOD 1–2–4 mg/ml+plant ceramides 1% (Inocosm), in NaCl 0.9%, according to the invention,
  plant ceramides 1% in NaCl 0.9% (control),
  liposomal bovine erythrocyte SOD 1–2–4 mg/ml, liposomes (control),
  gliadin extracted from wheat (control),
  bovine erythrocyte SOD+gliadin, according to the invention.

Subcutaneous administration:
  bovine erythrocyte SOD (Allerbiodose®) 0.5–1–2 mg/ml, in NaCl 0.9%,
  NaCl 0.9% (control),
  bovine erythrocyte SOD 0.5–1–2 mg/ml+plant ceramides 1% (Inocosm), in NaCl 0.9%, according to the invention,
  plant ceramides 1% in NaCl 0.9% (control),
  liposomal bovine erythrocyte SOD 0.5–1–2 mg/ml, liposomes (control),
  bovine erythrocyte SOD+gliadin, according to the invention.

Method

Prior treatment of the animals:

by oral administration: gavage

The gavage is performed on the animals (n=4) at T0 with a volume of 1 ml of solution or suspension to be studied, in 0.9% NaCl solution. This gavage is performed using a cannula mounted on a 1 ml syringe and introduced into the buccal cavity of the rat.

by subcutaneous administration:

The solutions or suspensions to be studied are administered at T0 by the injection of a volume of 0.3 ml (in 0.9% NaCl solution) behind the animal's head (n=4).

Each series of experiments is carried out on 4 animals per dose, the control groups always being treated in parallel for each experiment.

Catheterization of the carotid:

Once the gavage (or the subcutaneous injection) has been performed on the animals, the latter are anaesthetized by the slow intraperitoneal injection of thiopental (0.1 ml/100 g).

When the animal is asleep, it is placed on its back to allow catheterization of the carotid. This is done by carefully cutting the skin on the animal's neck with a pair of scissors.

The muscles are separated with forceps to give free access to the carotid.

The carotid is freed and then clamped at the heart end and ligated at the head end with a fine thread. A slight incision is then made in the carotid with a pair of scissors to allow the insertion of a catheter (over a distance of about 1.5 cm) mounted on a needle equipped with a one-way tap. The catheter is held in position by means of a second ligature at the heart end. It is then heparinated with the heparin solution in order to prevent any clotting of the blood when the successive samples are taken.

A compress of 0.9% NaCl solution is then placed over the wound to prevent it from drying out excessively.

The animals are warmed throughout the experiment by being placed under two lamps.

Blood sampling:

The samples are taken every hour for 6 hours (400 $\mu$l) via the one-way tap. The blood is collected in heparinated Eppendorf tubes (20 $\mu$l of heparin 1000 IU/ml). It is then centrifuged for 5 min at 4000 rpm. The plasma is then discarded and replaced with NaCl 0.9%. The tubes are centrifuged again for 5 min at 4000 rpm. The red blood cells are thus washed three times in succession.

Erythrocyte assays: measurement of the SOD activity:

The assays of the enzymatic activity of the erythrocyte SOD (of each form) are performed on each control or treated sample.

The erythrocytes are appropriately diluted in distilled water (+0.5 ml of 1% Triton solution) so that the inhibition obtained in the study tube is about 50% of that in the control tube.

The results obtained in IU SOD/ml are reported in IU SOD/mg haemoglobin. The haemoglobin is assayed by spectrophotometry at 405 nm.

Results

Figure 2:
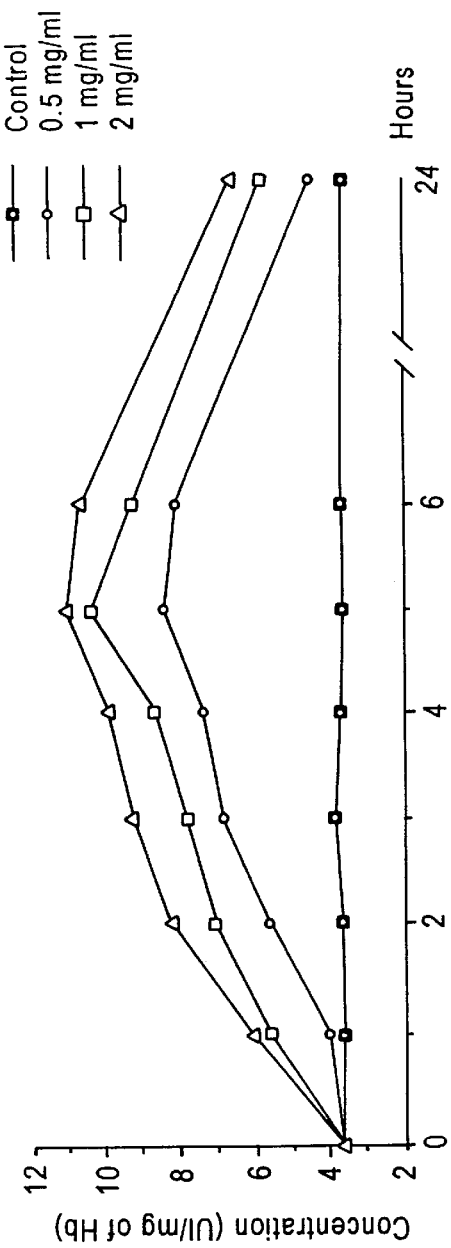

The results of the erythrocyte kinetics of the SOD administered subcutaneously are shown in FIGS. 1–3:

FIG. 1 corresponds to the erythrocyte concentrations obtained with free SOD,

FIG. 2 corresponds to the erythrocyte concentrations obtained with liposomal SOD, FIG. 3 corresponds to the results obtained with an SOD+ ceramide composition according to the invention.

Figures 5, 6:
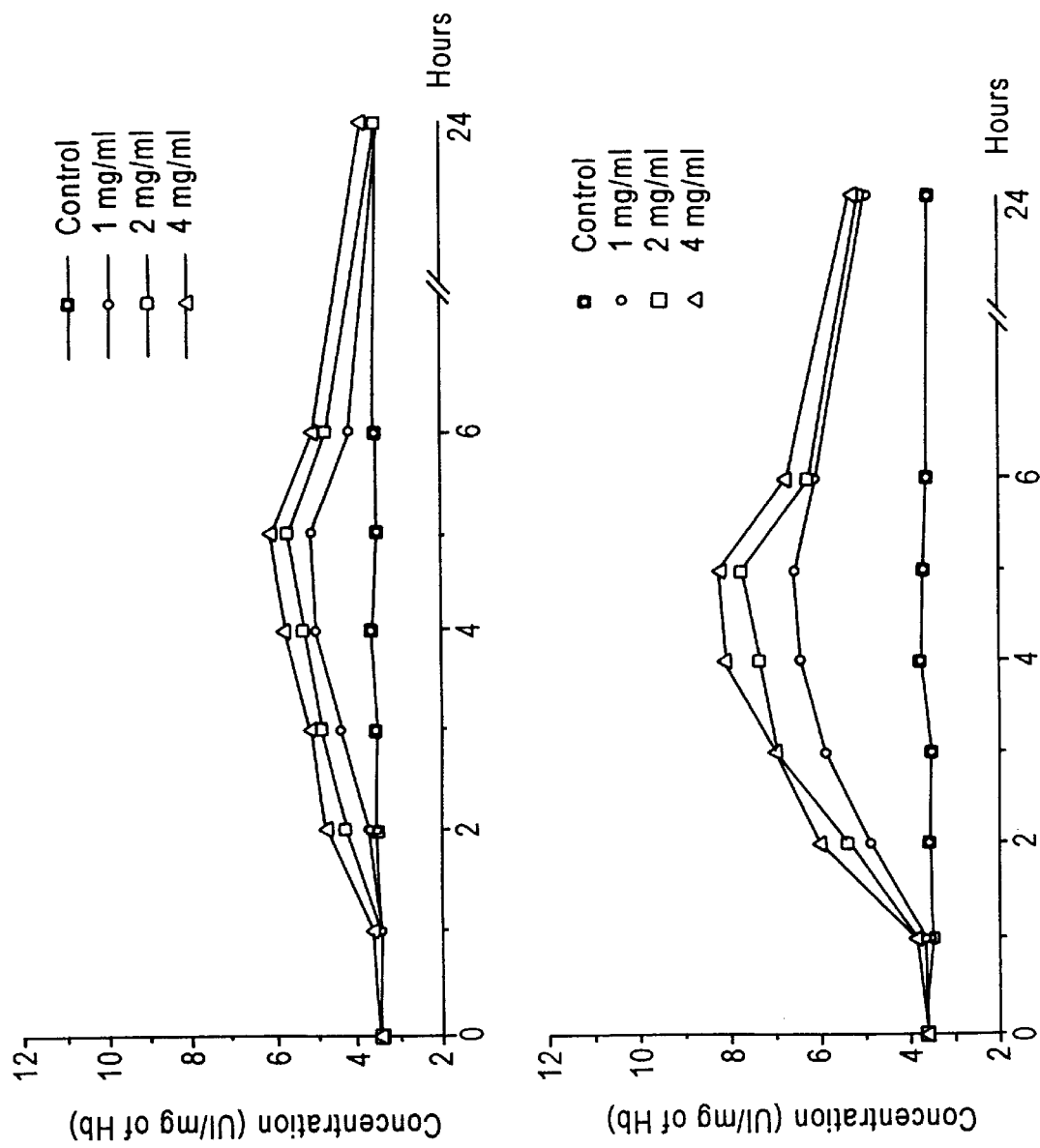
Figure 7:
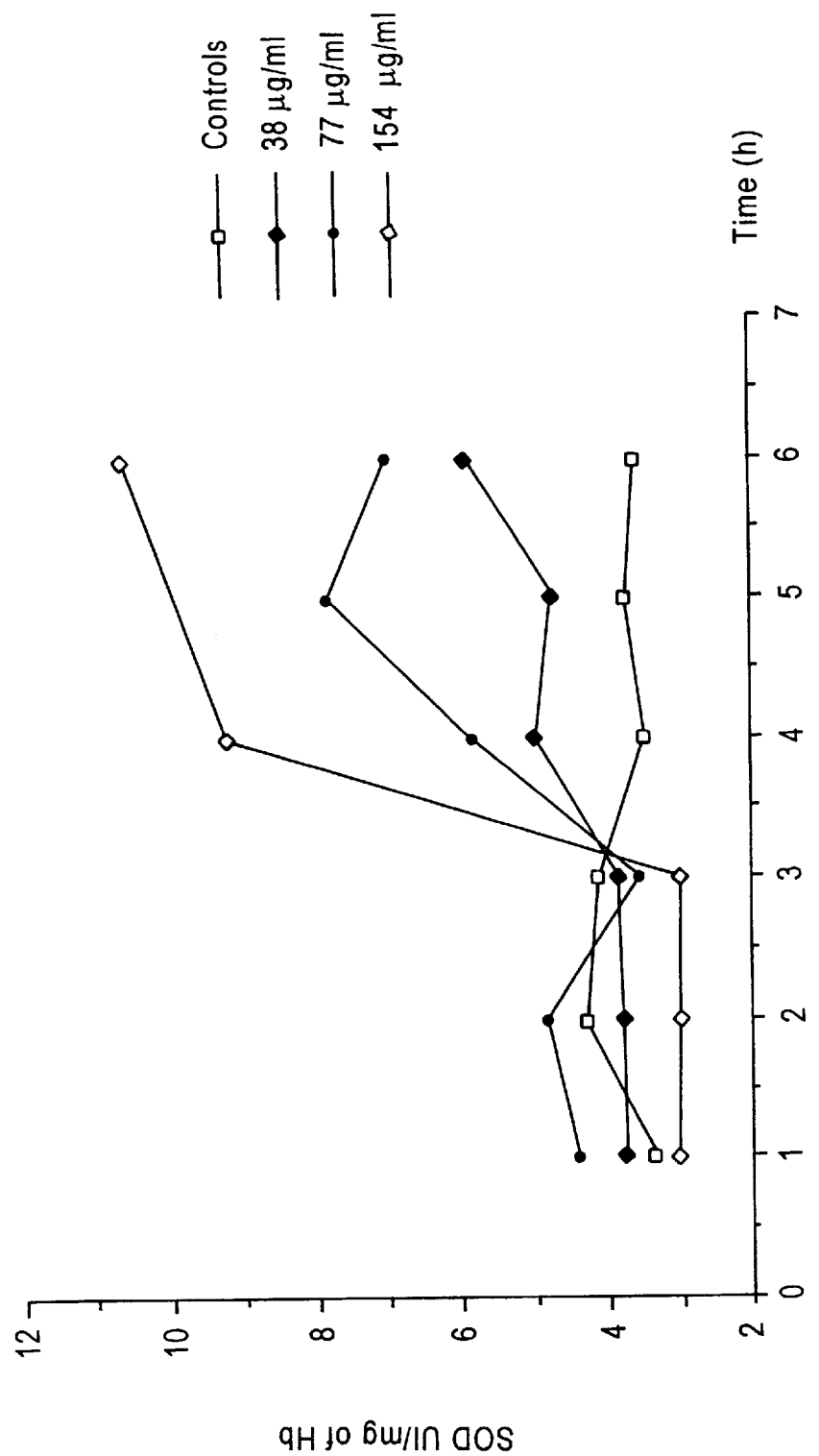

The results of the erythrocyte kinetics of the SOD administered orally are shown in FIGS. 4–7:

FIG. 4 corresponds to the erythrocyte concentrations obtained with free SOD,

FIG. 5 corresponds to the erythrocyte concentrations obtained with liposomal SOD, FIG. 6 corresponds to the erythrocyte concentrations obtained with an SOD+ceramide composition according to the invention, and FIG. 7 corresponds to the erythrocyte concentrations obtained with an SOD+gliadin composition according to the invention.

The Tables indicate the kinetics data obtained for the different curves shown.

TABLE I

AUC for the erythrocyte kinetics in rats after subcutaneous administration

| Kinetics curves | Concentrations | AUC (IU.h.mg$^{-1}$ of Hb) |
|---|---|---|
| SOD | 0.5 mg/ml | 42.36 |
|  | 1.0 mg/ml | 59.02 |
|  | 2.0 mg/ml | 80.88 |
| liposomal SOD | 0.5 mg/ml | 62.90 |
| (Example 2) | 1.0 mg/ml | 93.69 |
|  | 2.0 mg/ml | 118.73 |
| SOD + ceramides | 0.5 mg/ml | 62.28 |
| (Example 3) | 1.0 mg/ml | 91.86 |
|  | 2.0 mg/ml | 116.75 |

*amount administered: 0.3 ml

TABLE II

AUC for the erythrocyte kinetics in rats after oral administration

| Kinetics curves | Concentrations (mg/ml) | AUC (IU.h.mg$^1$ of Hb) | F' (relative bioavailability/SC) |
|---|---|---|---|
| SOD | 1.0 | 2.13 | 0.05 |
|  | 2.0 | 7.97 | 0.13 |
|  | 4.0 | 12.09 | 0.15 |
|  | 1.0 | 9.90 | 0.16 |
| liposomal SOD | 2.0 | 17.24 | 0.18 |
| (Example 2) | 4.0 | 25.87 | 0.22 |
| SOD + | 1.0 | 45.43 | 0.73 |
| ceramides | 2.0 | 52.16 | 0.56 |
| (Example 3) | 4.0 | 61.01 | 0.52 |
| SOD + gliadan | 1.0 | >20 | ND |
| (Example 1) | 2.0 | >50 | ND |
|  | 4.0 | >100 | ND |

ND = not determinable

5. Conclusion

Subcutaneous administration:

The $T_{max}$ are around 5 hours for the 4 forms of SOD.

The $C_{max}$ are slightly lower for the free form and identical for the liposomal form and the form with ceramides.

The $C_{max}$ obtained with SOD+gliadin are 6.52 for a concentration of 25 µg/ml, 7.48 for a concentration of 50 µg/ml and 65.68 for a concentration of 100 µg/ml.

Oral administration:

The $T_{max}$ are around 5 hours for free SOD and the compositions according to Examples 2 and 3, whereas $T_{max}$ for the formulation based on gliadin (Example 1) is greater than 6 h.

The $C_{max}$ are lower for the free form, intermediate for the liposomal form (Example 2) and higher for the form with ceramides or gliadin (Examples 1 and 3).

The SOD therefore reaches high concentrations when administered orally and its passage is significantly favoured when a composition according to the invention is used.

EXAMPLE 5

Anti-Inflammatory Properties of Superoxide Dismutase by Oral Administration

A. Paw Oedema

1) Object of the study:

To study the comparative kinetics of the anti-inflammatory action of a free form of SOD and a composition according to the invention, at different concentrations.

2) Solutions or suspension studied (cf. Example 4):

Free SOD

NaCl control

SOD+ceramides (according to Example 3)

Ceramide control

3) Technique

Treatment of the animals with SOD:

Gavage of the animals with the aid of a cannula mounted on a 0.5 ml syringe inserted in the buccal cavity of the rat, as described in Example 5.

2 gavages are performed per day (morning and evening).

Induction of the oedema:

Injection of 0.1 ml of λ carrageenan 1% in the paw pad.

Measurement of the paw volume:

The measurements are made every hour for 6 hours.

Figure 8:
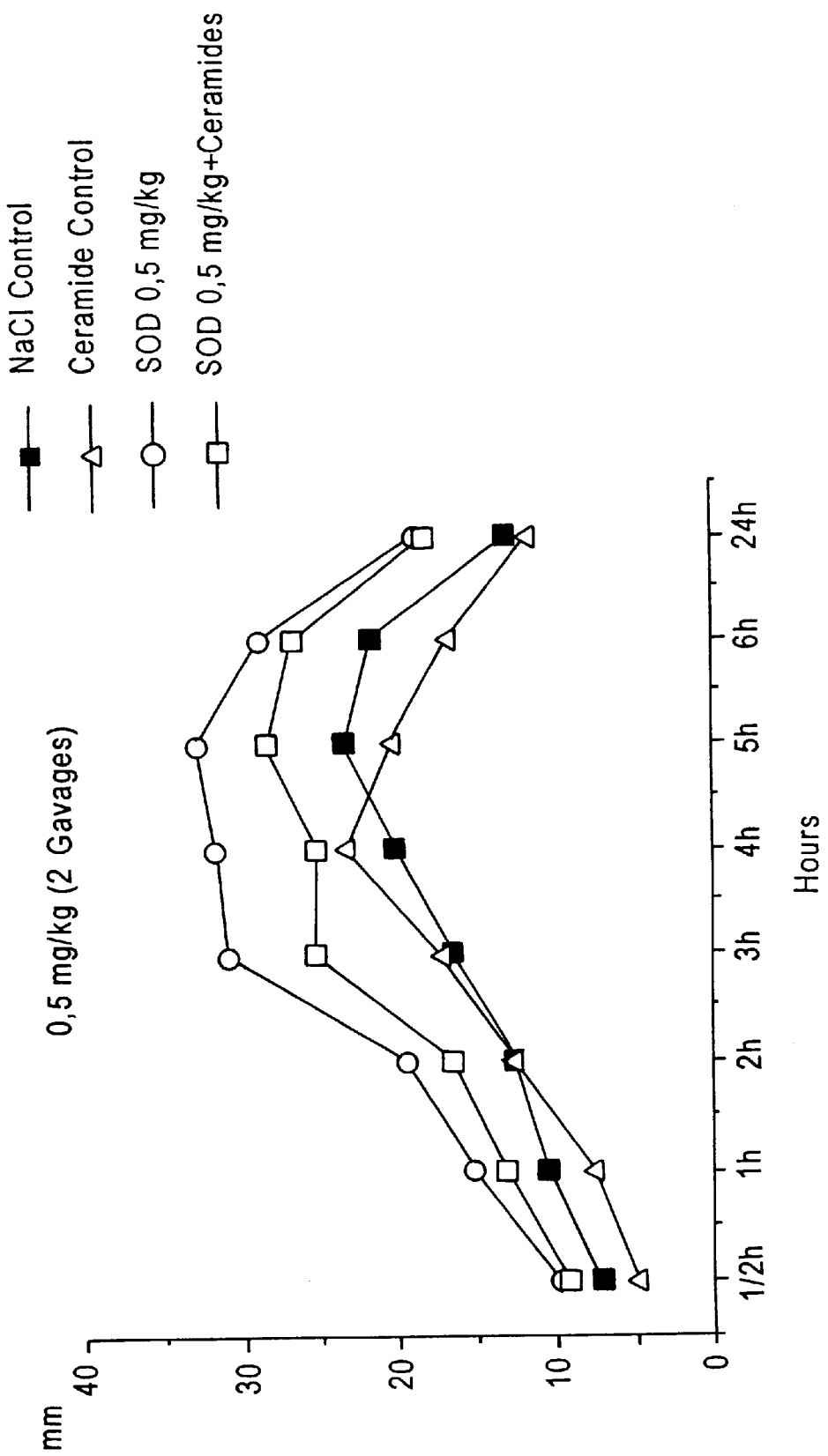
FIGS. 8 to 15 illustrate the results of treatment with a composition according to the invention (anti-inflammatory properties obtained after oral administration) on the volume of rat paw oedema (inflammation standard) as a function of the amount of SOD administered.
Figure 9:
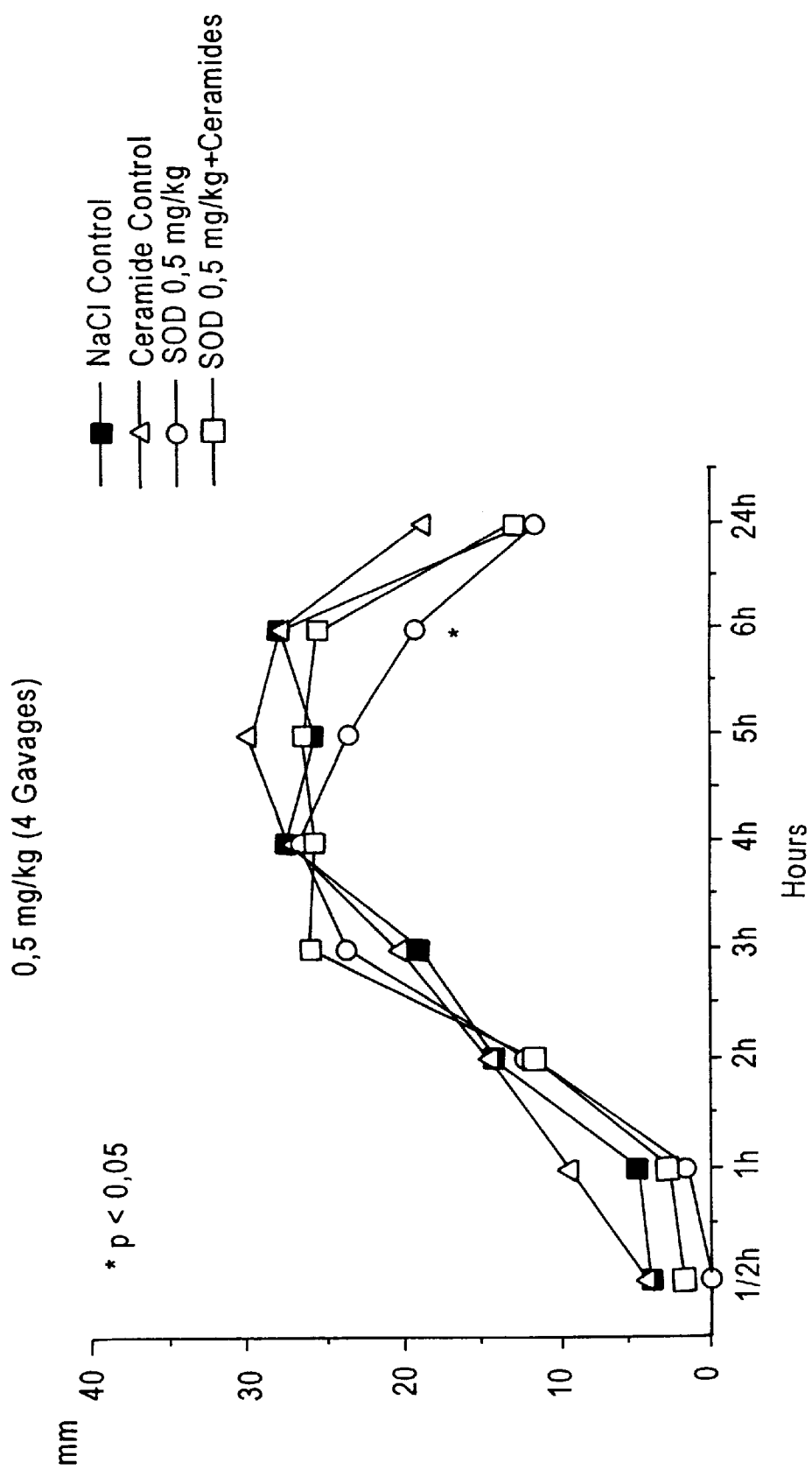
Figure 10:
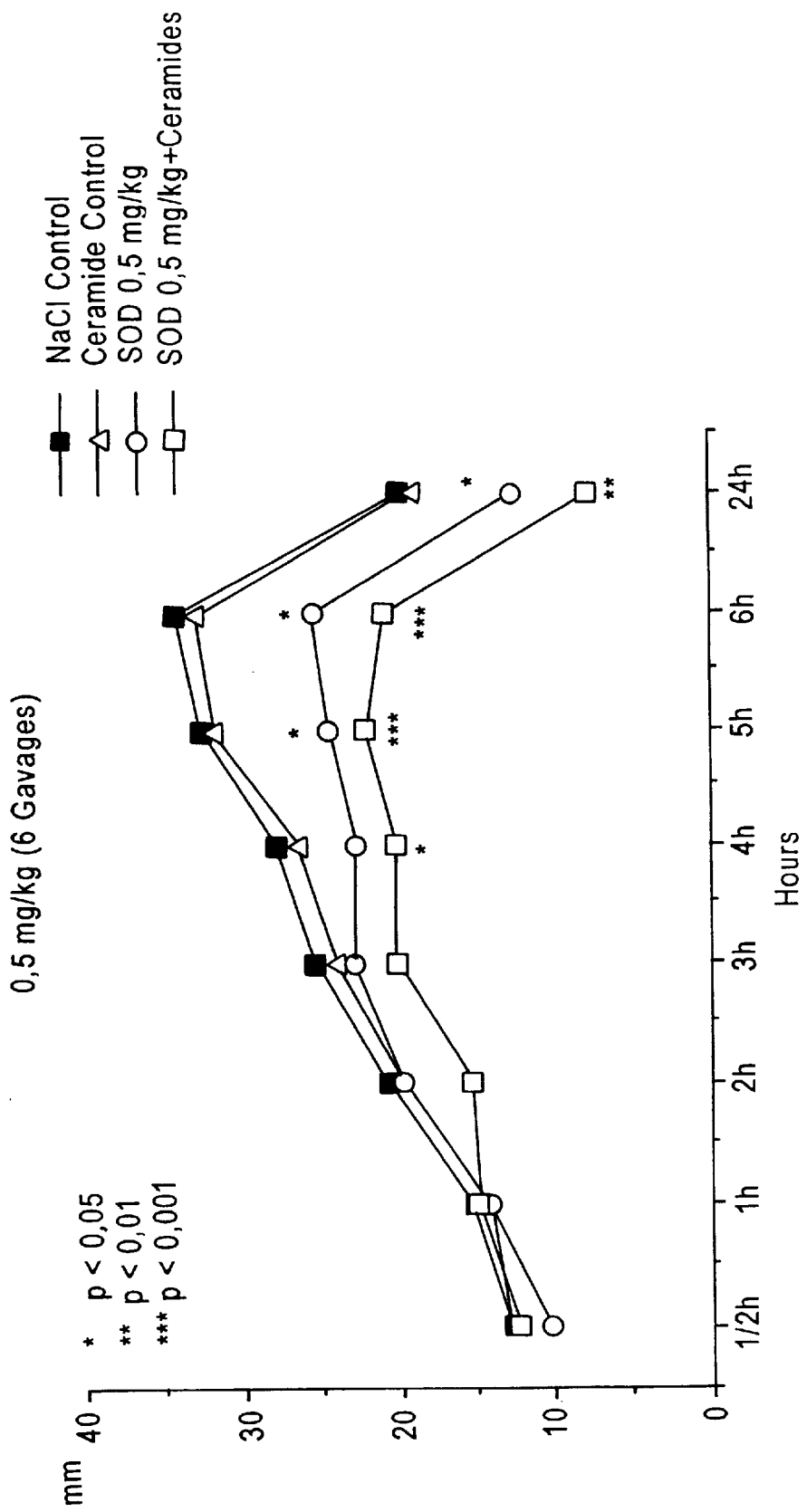
Figure 11:
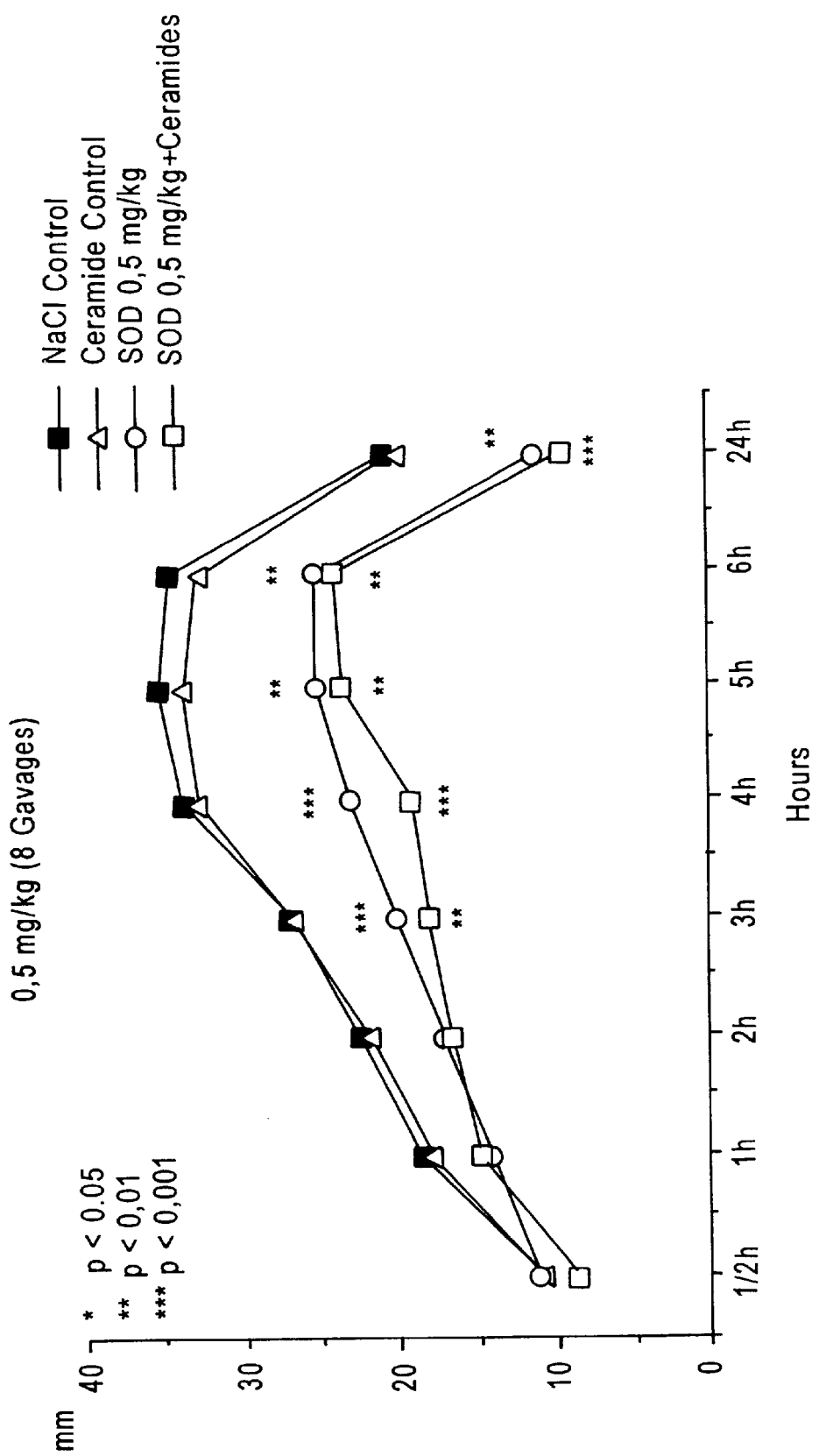
Figure 12:
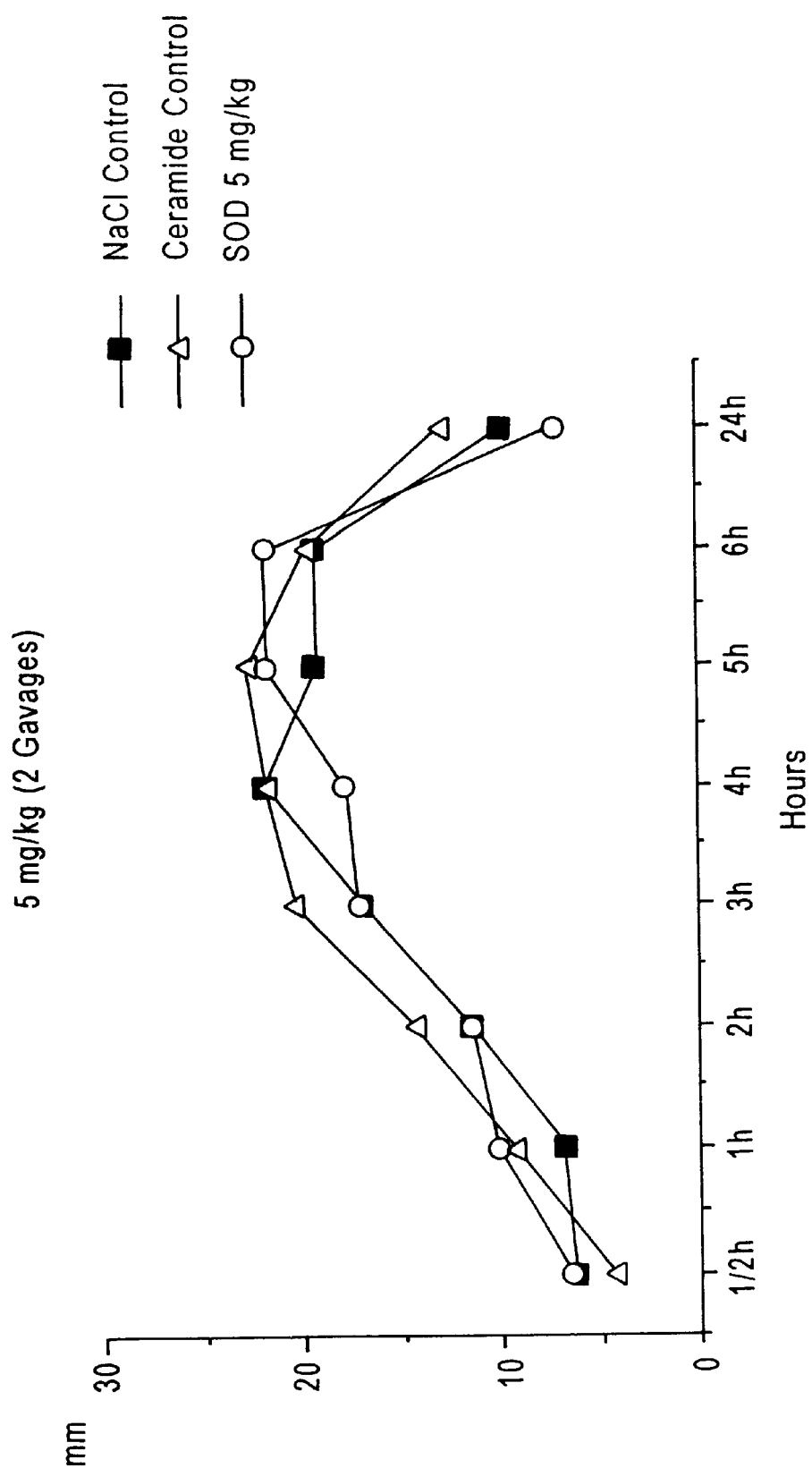
Figure 13:
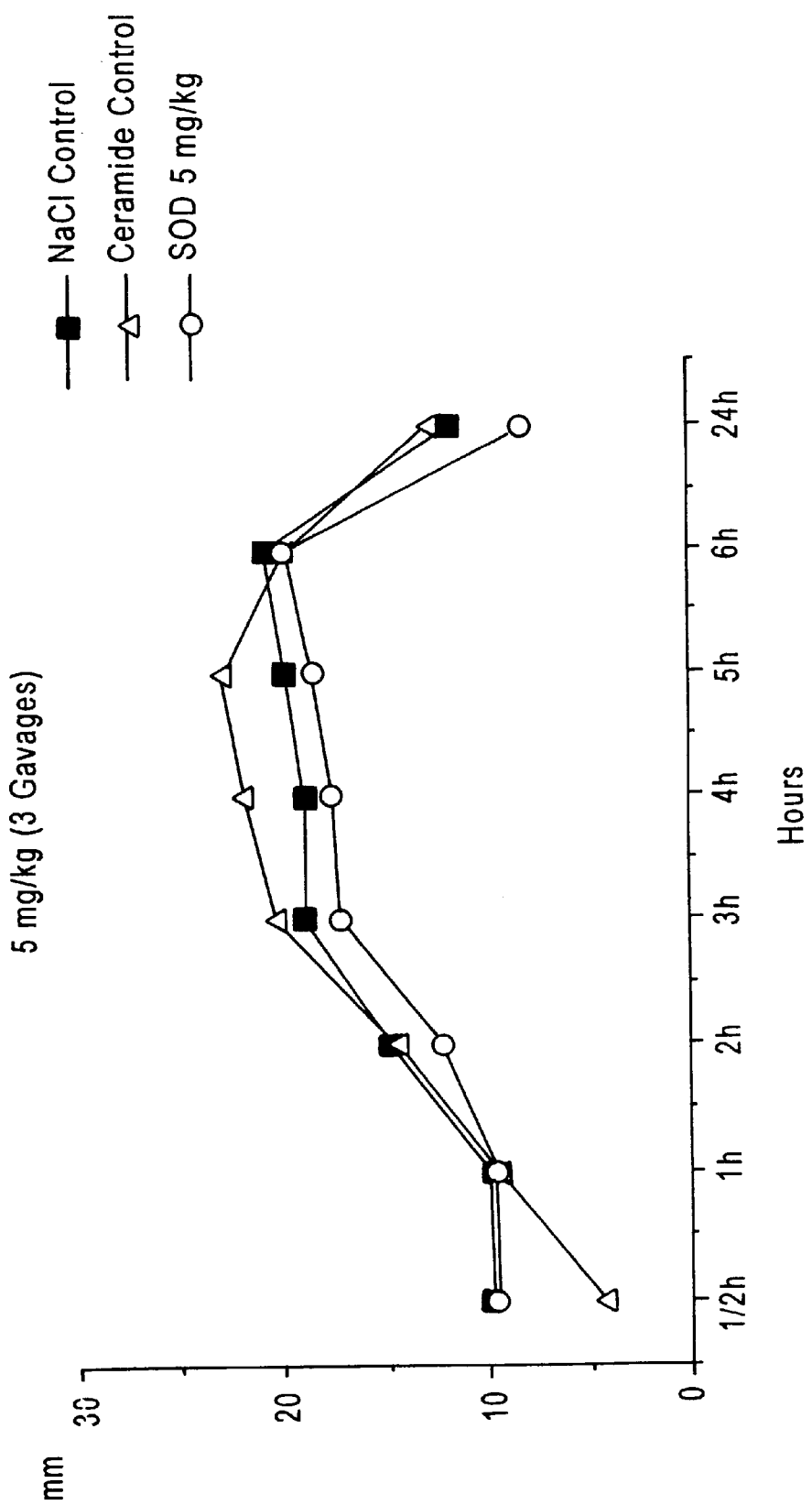
Figure 14:
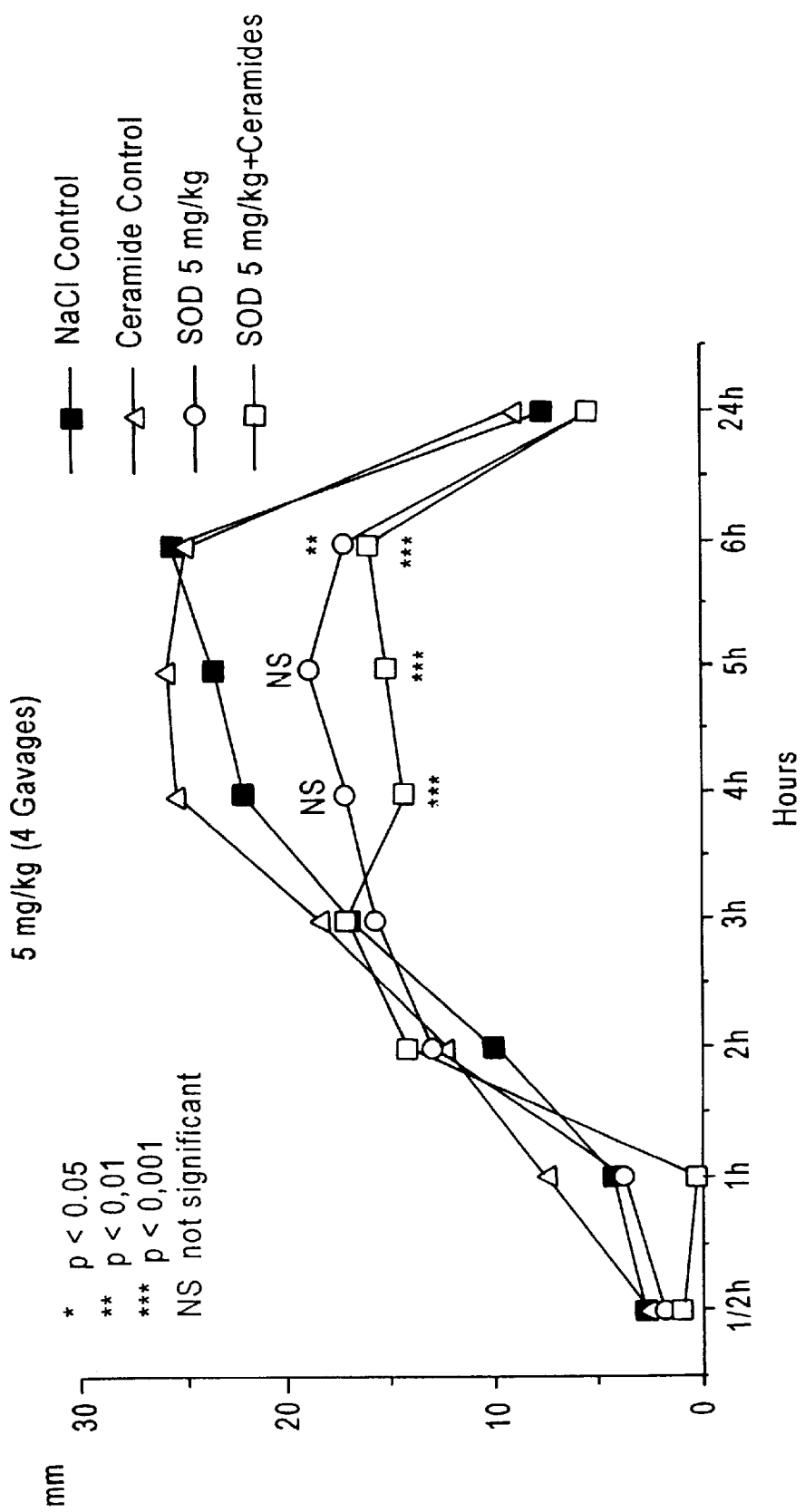
Figure 15:
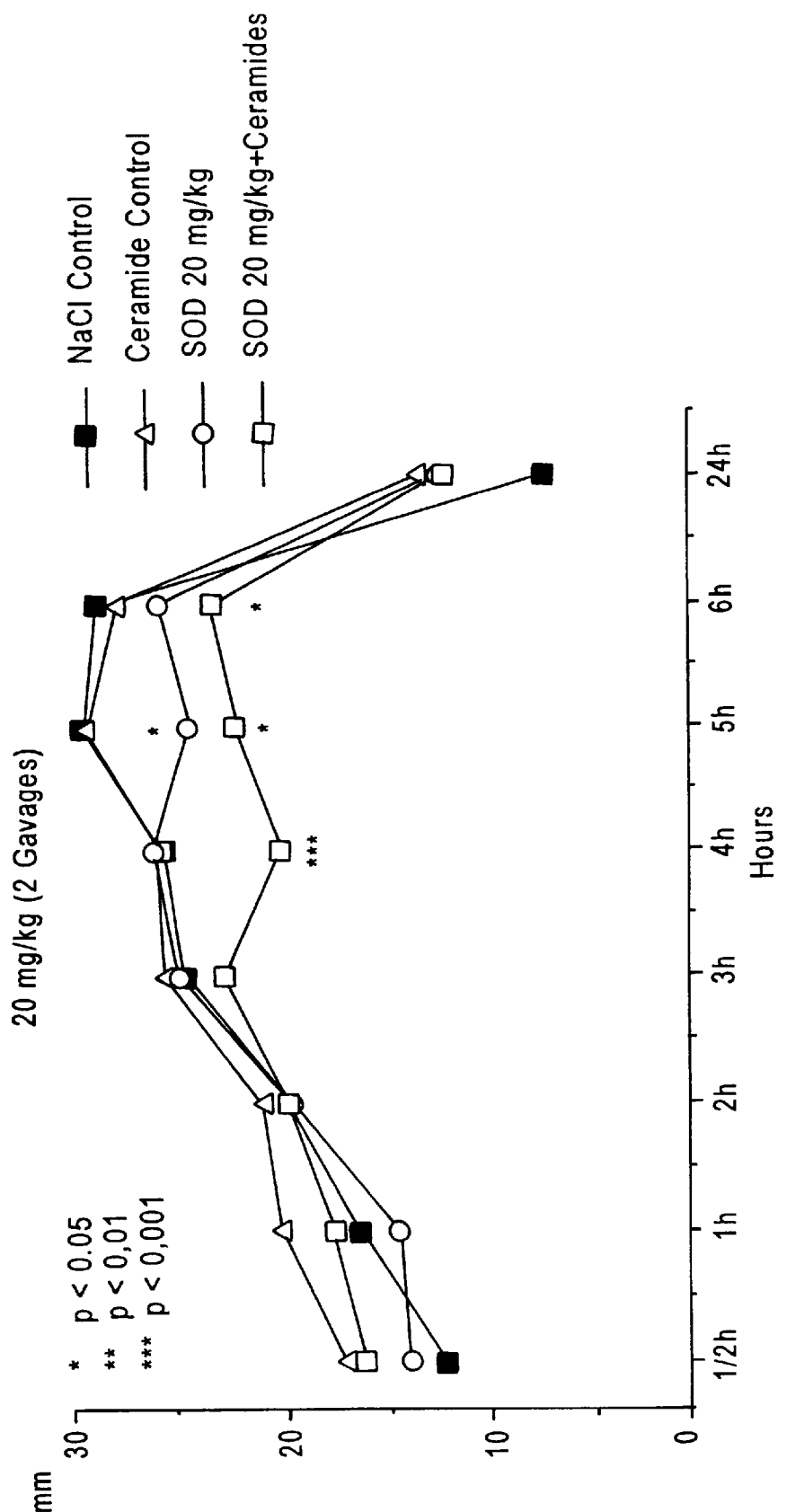

FIGS. 8 to 15 illustrate the results of treatment with a composition according to the invention (anti-inflammatory properties) on the volume of rat paw oedema (inflammation standard) as a function of the amount of SOD administered:

FIG. 8 corresponds to the results obtained with 0.5 mg/kg of SOD (2 gavages),

FIG. 9 corresponds to the results obtained with 0.5 mg/kg of SOD (4 gavages),

FIG. 10 corresponds to the results obtained with 0.5 mg/kg of SOD (6 gavages),

FIG. 11 corresponds to the results obtained with 0.5 mg/kg of SOD (8 gavages),

FIG. 12 corresponds to the results obtained with 5 mg/kg of SOD (2 gavages),

FIG. 13 corresponds to the results obtained with 5 mg/kg of SOD (3 gavages),

FIG. 14 corresponds to the results obtained with 5 mg/kg of SOD (4 gavages), and FIG. 15 corresponds to the results obtained with 20 mg/kg of SOD (2 gavages).

Figure 16:
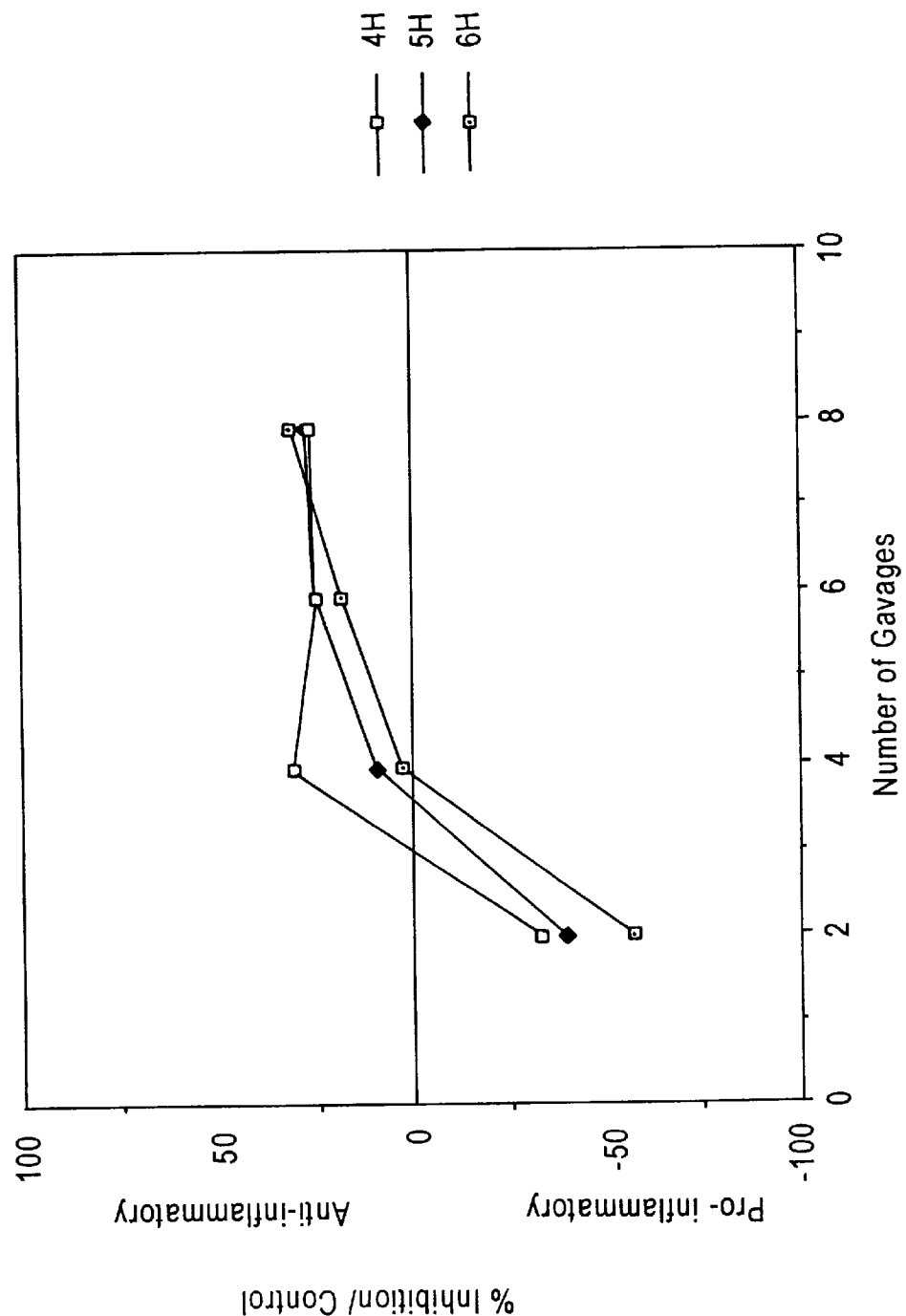
FIGS. 16 and 17 illustrate the relationship between the amount of SOD administered orally and the anti-inflammatory effect (percentage inhibition of the SOD as a function of the number of gavages); the paw oedemas are measured 4 h, 5 h and 6 h after the gavages.
Figure 17:
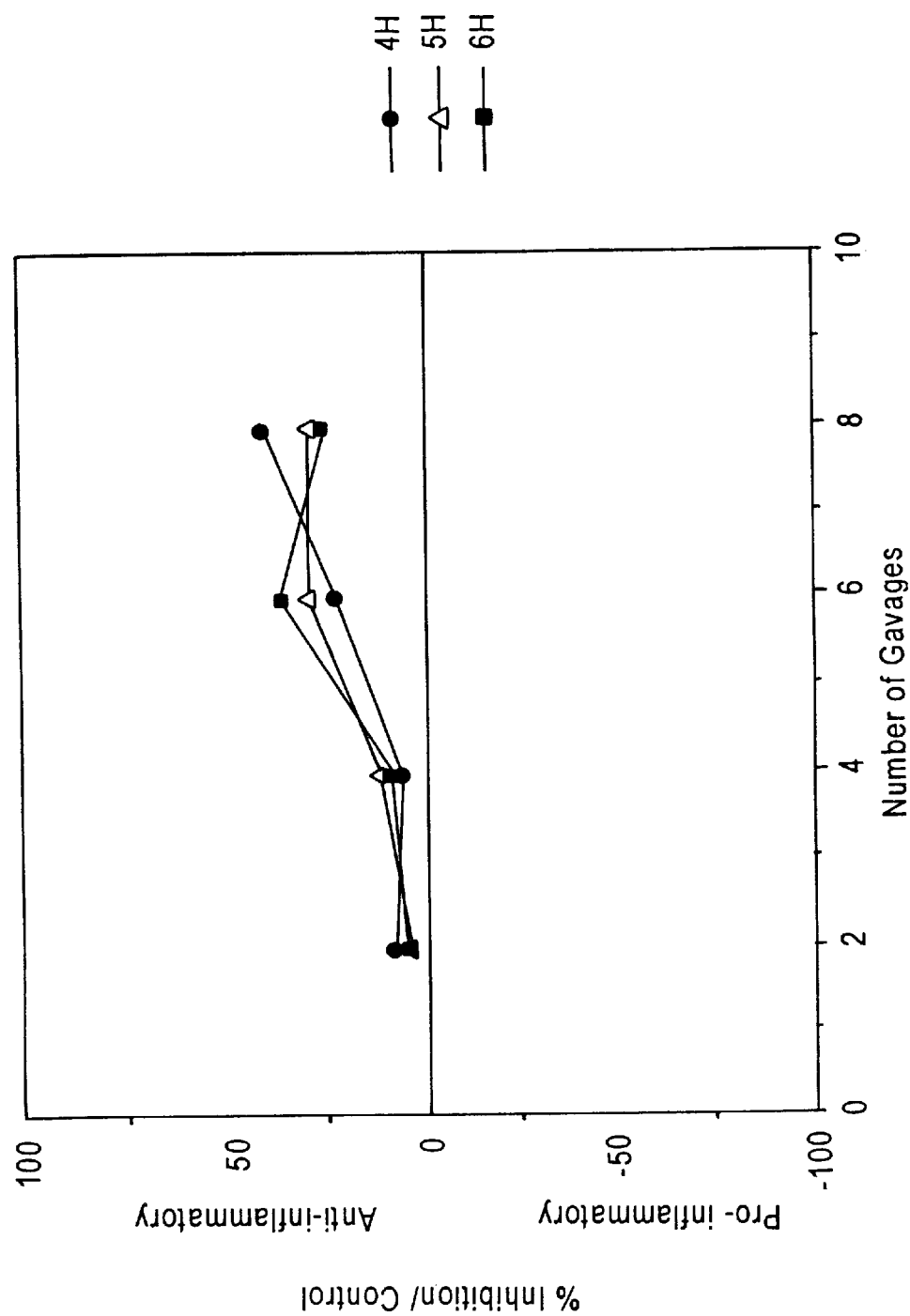

Within the framework of the same protocol, FIGS. 16 and 17 illustrate the percentage inhibition of the SOD as a function of the number of gavages:

FIG. 16 corresponds to the percentage inhibition obtained with 0.5 mg/kg of SOD, FIG. 17 corresponds to the percentage inhibition obtained with 0.5 mg/kg of SOD+ceramides.

The results obtained show the advantage of encapsulating the SOD in terms of pharmacological activity by oral administration, even though an anti-inflammatory action is demonstrated at the same doses as from 4 or 6 gavages in the case of the free SOD.

The encapsulated form of SOD always exhibits an anti-inflammatory effect, irrespective of the number of gavages.

B. Study of Granulocyte Activation

1) Object of the study

To compare the inhibitory effect of different forms of SOD on granulocyte activation.

2) Solutions or suspensions studied

Same solutions or suspensions as in Example 5 A.

3) Technique

Sampling:

The samples are those collected 3 hours after pleurisy.

Assay:

Reagent control: PBS$^+$ (0.65 ml)+cytochrome C 5 mg/ml (0.15 ml).

Cell control: PBS$^+$ (0.65 ml)+cytochrome C 5 mg/ml (0.15 ml)+G 10 M/ml (0.2 ml).

Test: PBS$^+$ (0.45 ml)+cytochrome C 5 mg/ml (0.15 ml)+ZO or PMA (0.2 ml), with: NaCl control (column 1), SOD (column 2), Ceramide control (column 3), SOD+ ceramides (column 4), Liposome control (column 5), Liposomal SOD (column 6).

Incubate for 15 minutes in a water bath at 37° C., with shaking, stop the reaction for 10 minutes in an ice bath, centrifuge for 5 minutes at 2000 rpm.

4) Results

Figure 18:
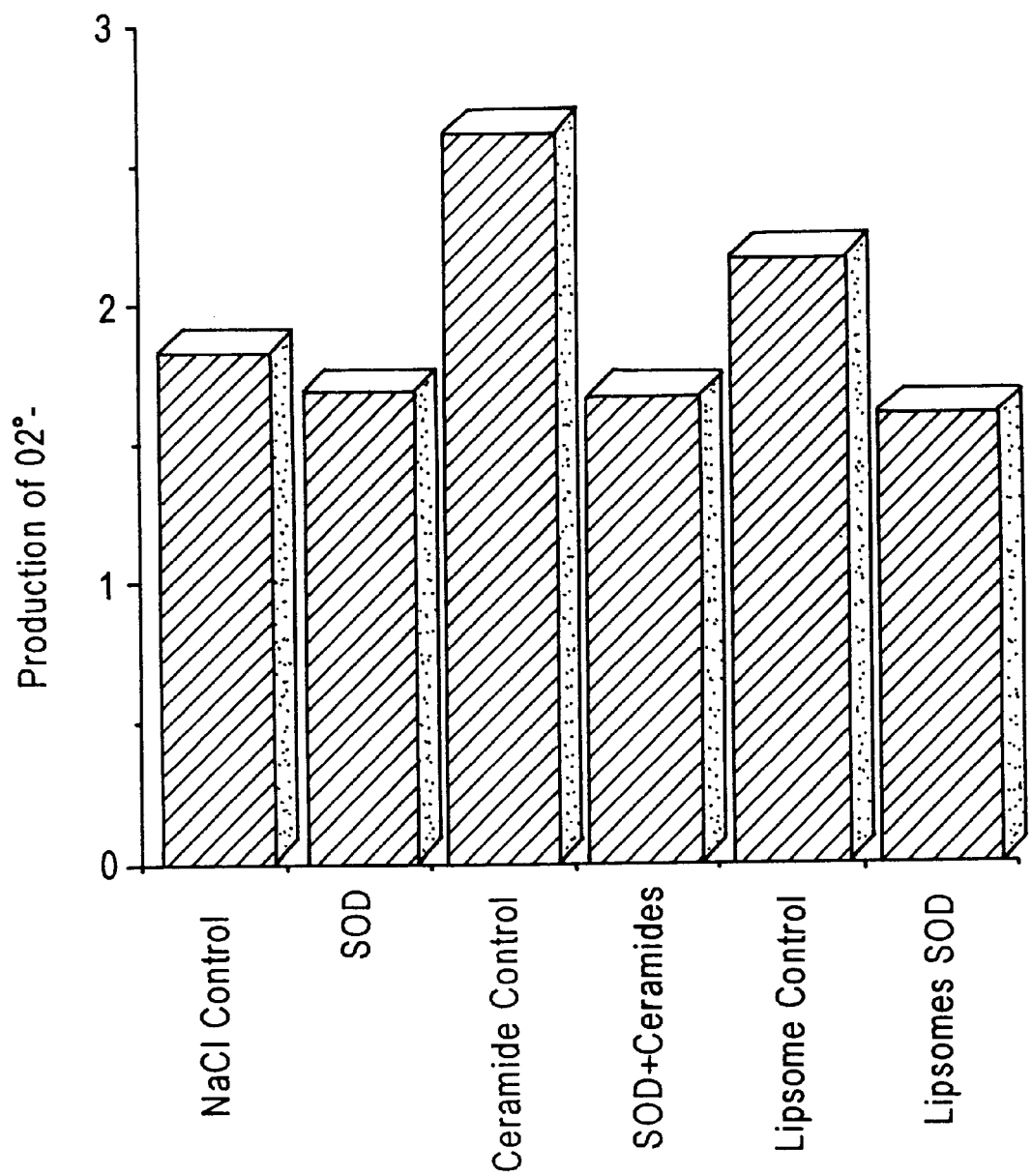
FIGS. 18 to 20 illustrate the inhibitory effect of the oral administration of SOD on granulocyte activation and the significant increase in bioavailability with a composition according to the invention.
Figure 19:
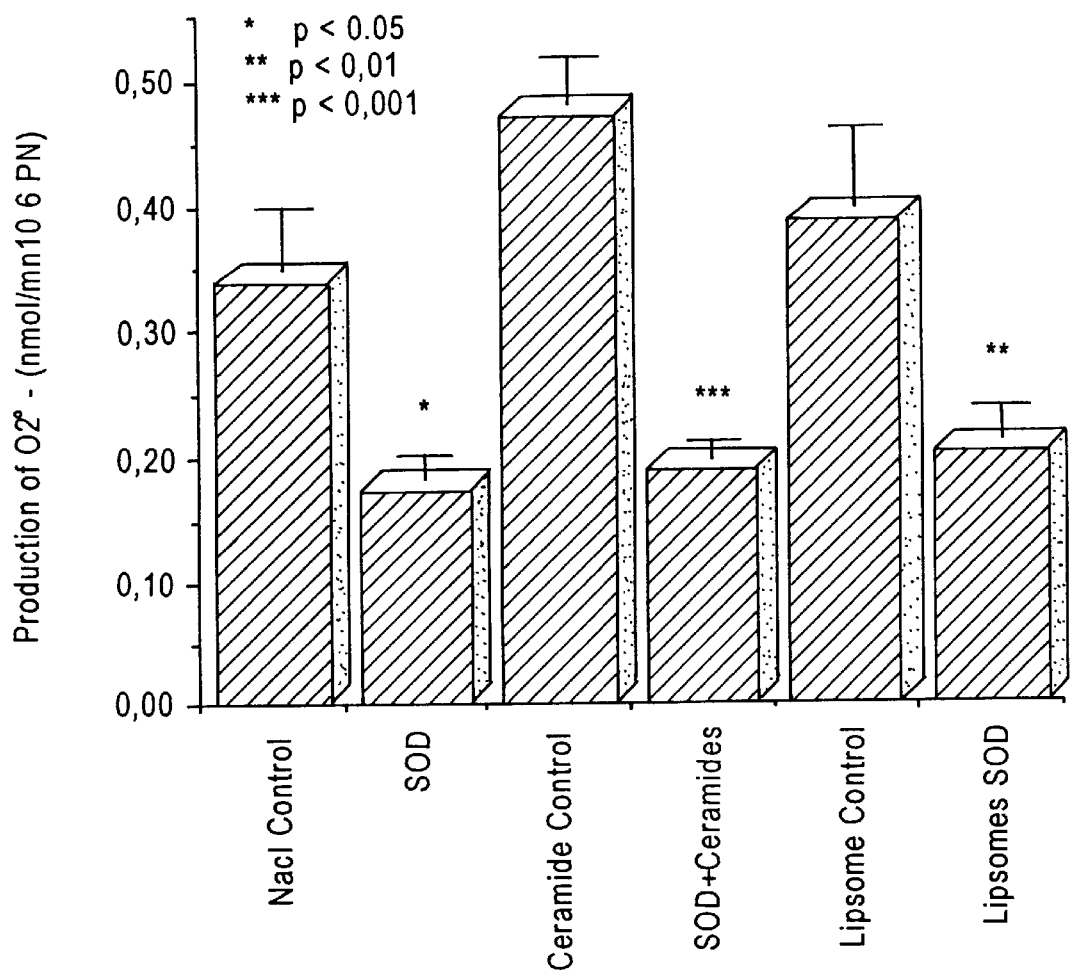
Figure 20:
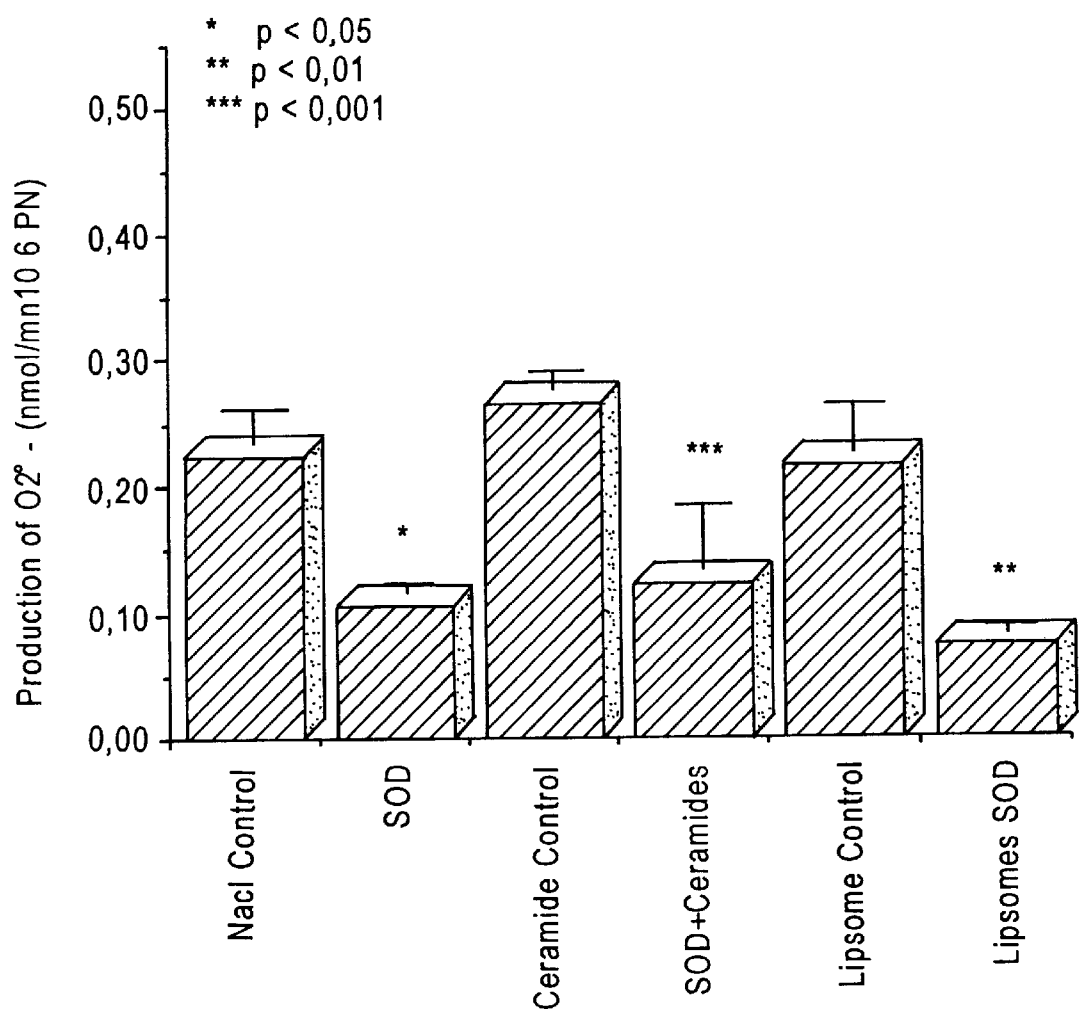

FIGS. 18 to 20 illustrate the results obtained:

FIG. 18 shows the production of superoxide anions by the granulocytes after stimulation, FIG. 19 shows the production of superoxide anions by the granulocytes after stimulation with zymosan (spectrophotometric technique), FIG. 20 shows the production of superoxide anions by the granulocytes after stimulation with PMA (spectrophotometric technique).

The results significantly show the anti-inflammatory role, by oral administration, of free SOD ($P<0.05$), SOD encapsulated in liposomes ($P<0.07$) and SOD encapsulated in ceramides ($P<0.001$).

FIG. 17 demonstrates that, at a dose of 0.5 mg/kg, the anti-inflammatory effect of free SOD is observed as from 4 gavages, whereas the results of FIG. 18 demonstrate that SOD encapsulated in ceramides has an anti-inflammatory effect as from the second gavage.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. Pharmaceutical compositions consisting essentially of in combination a single phase physical mixture of a superoxide dismutase and at least one compound selected from the group consisting of prolamines and polymer films derived from said prolamines.

2. Composition according to claim 1 wherein said prolamines are of vegetable origin and are derived from at least one cereals selected from the group consisting of wheat, rye, barley, oats, rice, millet and maize.

3. A pharmaceutical composition consisting essentially of a single phase mixture of a combination of a superoxide dismutase and a hydrophobic polymer comprising at least one prolamine of vegetable origin, and wherein said prolamine is admixed with:

(i) at least one plasticizer selected from the group consisting of polyols and esters selected from the group consisting of polyols, phthalates, adipates, sebacates, phosphates, citrates, tartrates and malates, and wherein the ratio of prolamine to plasticizer is between 2:1 and 2:0.5, and (ii) 5 to 30% of at least one solvent selected from the group consisting of monools, diols and water, and wherein said composition is obtained by evaporating at least part of the solvent present in a starting composition comprising:

40 to 80% of at least one prolamine dissolved in an aqueous-alcoholic solvent having a volume of alcohol to volume of water of 40 to 80%, and at least one plasticizer, wherein the ratio of plasticizer to alcoholic prolamine solution is 0.10:1 to 0.50:1;

until a homogeneous solution of a predetermined thickness is obtained.

4. Composition according to claim 1 further comprising at least one pharmaceutically acceptable vehicle.

5. Composition as claimed in claim 2 wherein said prolamines are derived from wheat flour.

6. The composition according to claim 3, wherein said ratio of plasticizer to alcoholic prolamine solution is between 0.20:1 and 0.23:1.

7. A method of treating inflammation in an animal having such inflammation comprising administering to said animal an effective quantity of a composition as claimed in claim 1.

8. The method as claimed in claim 7 wherein said animal is a human.

9. A method of treating inflammation in an animal having such inflammation comprising administering to said animal an effective quantity of a composition as claimed in claim 3.

10. The method as claimed in claim 9 wherein said animal is a human.

* * * * *